(12) United States Patent
Guthrie et al.

(10) Patent No.: US 9,470,624 B2
(45) Date of Patent: Oct. 18, 2016

(54) IMAGE CAPTURE AND LIGHTING APPARATUS

(75) Inventors: Lusia Halina Guthrie, Dulwich (AU); John Hughes Glasson, Adelaide (AU); Graeme John Bullock, Doncaster (AU); Graeme Cross, Fitzroy (AU); Rhys Ernst Hill, Adelaide (AU)

(73) Assignee: LBT Innovations Limited, Adelaide, South, Australia (AU)

(*) Notice: Subject to any disclaimer, the term of this patent is extended or adjusted under 35 U.S.C. 154(b) by 4 days.

(21) Appl. No.: 14/002,703

(22) PCT Filed: Mar. 2, 2012

(86) PCT No.: PCT/AU2012/000210
§ 371 (c)(1),
(2), (4) Date: Apr. 7, 2014

(87) PCT Pub. No.: WO2012/119190
PCT Pub. Date: Sep. 13, 2012

(65) Prior Publication Data
US 2014/0227774 A1      Aug. 14, 2014

(30) Foreign Application Priority Data

Mar. 4, 2011   (AU) ................................ 2011900784

(51) Int. Cl.
*C12M 1/34*   (2006.01)
*G01N 33/483*   (2006.01)
*G01N 21/25*   (2006.01)

(52) U.S. Cl.
CPC ............ *G01N 21/255* (2013.01); *C12M 41/36* (2013.01); *G01N 33/4833* (2013.01)

(58) Field of Classification Search
CPC ............................ C12M 41/36; G01N 21/255
USPC .......................................................... 435/288
See application file for complete search history.

(56) References Cited

U.S. PATENT DOCUMENTS

| 5,545,561 A | 8/1996 | Lleonart |
| 2005/0051723 A1* | 3/2005 | Neagle et al. ................. 250/306 |

(Continued)

FOREIGN PATENT DOCUMENTS

| CN | 201007773 Y | 1/2008 |
| GB | 2 346 893 A | 8/2000 |
| GB | 2346893 A | 8/2000 |

(Continued)

OTHER PUBLICATIONS

English Translation of Document No. CN 201007773 Y provided by proquest.com: Bacteria colonies and bacteriostatic circle dark background imaging system; Jan. 16, 2008.*

(Continued)

*Primary Examiner* — Kevin Joyner
*Assistant Examiner* — Holly Mull
(74) *Attorney, Agent, or Firm* — Inskeep IP Group, Inc.

(57) ABSTRACT

An apparatus for use in analysing microbial growth on a solid culture medium in a culture plate, the apparatus including an image capture device, a support for supporting the culture plate for the image capture device to capture an image of the solid culture medium and any microbial growth, a ring light between the image capture device and the support, for diffusely illuminating one side of the culture plate, and a frame for positioning the image capture device, support and ring light relative to each other.

20 Claims, 5 Drawing Sheets

(56) References Cited

U.S. PATENT DOCUMENTS

| | | | |
|---|---|---|---|
| 2006/0166305 A1 | 7/2006 | Jiang et al. | |
| 2008/0266653 A1* | 10/2008 | Korpinen | G02B 21/26 359/368 |
| 2009/0135603 A1 | 5/2009 | Graessle | |
| 2009/0152474 A1* | 6/2009 | Berger et al. | 250/484.4 |
| 2010/0166271 A1* | 7/2010 | Nishida | C12Q 1/06 382/128 |

FOREIGN PATENT DOCUMENTS

| | | | |
|---|---|---|---|
| JP | H07-500505 | | 1/1995 |
| JP | 9318506 A | * | 12/1997 |
| JP | 2001-525162 A | | 12/2001 |
| JP | 2006-508362 | | 3/2006 |

OTHER PUBLICATIONS

English Translation of Document No. JP 9318506 A provided by Japan Platform for Patent Information (www.j-platpat.inpit.go.jp).*
WIPO, Australian International Search Authority, International Search Report mailed Apr. 11, 2012 in International Patent Application No. PCT/AU2012/000210, 4 pages.
Japanese Patent Office, Notice of Reasons for Rejection in Japanese Patent Application No. 2013555706, 2 pages.
The State Intellectual Property Office of P.R. China, Office Action in Chinese Patent Application No. 201280021476.2, 11 pages.
European Patent Office, Supplementary European Search Report in European Patent Application No. 12755407, 10 pages.

* cited by examiner

IMAGE CAPTURE AND LIGHTING APPARATUS

RELATED APPLICATIONS

This application claims priority to and is the U.S. National Phase of international patent application number PCT/AU2012/000210, International Filing Date 2 Mar. 2012, entitled Image Capture And Lighting Apparatus, which claims priority to Australian Provisional Patent Application No. 2011900784 filed on 4 Mar. 2011, entitled Image Capture And Lighting Apparatus, both of which are incorporated herein by reference in their entireties.

This application claims priority from Australian Provisional Patent Application No. 2011900784 filed on 4 Mar. 2011, the contents of which are to be taken as incorporated herein by this reference.

FIELD OF THE INVENTION

The present invention relates to an image capture and lighting apparatus for use in analysing microbial growth on a solid culture medium, particularly microbial growth in the form of isolated bacterial colonies grown following the inoculation and incubation of the a solid culture medium with a microbiological sample. It is envisaged that the image capture and lighting apparatus of the present invention will find use in a microbiological laboratory.

BACKGROUND TO THE INVENTION

The isolation of individual colonies of micro-organisms (and in particular bacteria) is an important procedure in many microbiological laboratories. This isolation of bacteria is normally done either manually by skilled laboratory technologist or automatically by robotic streaking equipment. In either case, a microbiological sample is first dispensed upon the surface of a solid culture medium followed by the spreading of the microbiological sample across the surface of the medium (called "streaking"). Typically, multiple streaks are made of increasing dilution of the inoculum across the solid culture medium.

The streaks of increasing dilution tend to provide, generally towards the tail of the streaks, a number of single cells that allow for the growth of isolated microbiological colonies after incubation. These isolated colonies may then be analysed for various physical features e.g. colony morphology, and may undergo staining and other procedures which may be necessary for determining, for example, the genus, the species and/or the strain of the previously unidentified organism in the microbiological sample.

Traditionally, this analysis has been carried out visually in a microbiological laboratory by skilled technologists, resulting in the technologist making a microbiological assessment. This assessment may include the detection of the presence or absence of bacterial colonies, the detection of colour(s) of each colony type, the mapping of colour distribution to determine the presence of variations in colour which could be attributed to fermentation or haemolysis, the differentiation between confluent and isolated colony growth, the measurement of colony texture or viscosity, and the determination of two-dimensional and three-dimensional shape, and/or enumeration of the different types of colonies.

Where growth of potentially pathogenic bacteria is identified, the solid culture medium is progressed to the next step of the laboratory workflow and becomes the subject of further confirmatory identification and antibiotic susceptibility testing, in line with current regulatory requirements.

Over the years, there has been some efforts, for example, to capture images (either still or video, and in either analogue or digital forms) of bacterial colonies so that the technologist is able to more efficiently view a higher number of surfaces using visual aids such as monitors, microscopes, colony counters and/or computers.

It is important that these images are captured accurately, as the colour, shape and texture of the bacterial colonies, and the colour of the solid culture medium are used in identifying, for example, the bacteria type. Many commercial solid culture mediums, such as agars, are initially of various colours and transparencies and some are almost totally opaque (e.g. Methicillin-Resistant *Staphylococcus aureus* (MRSA) identification agars). Some plates are split into two halves, so that each side of the plate has a different type (and potentially colour) of agar. Also, the bacterial colonies can be of different colours, shapes and textures. Some are simple round spots, others swarm in continuous waves across the agar surface and some have characteristic surface topography such as dimples or a granular texture. The effect of the bacterial colonies on the colour indicators blended in the agar formulation can, for example, produce a strong colour reaction, such as blue halo around colonies of MRSA on specific indicator agar or colour reaction resulting from pH changes caused by bacterial growth on agar containing appropriate indicator compounds, such as neutral red. In another example, further colour changes are visible in blood agars, immediately below and around colonies which are able to damage or destroy red blood cells via haemolysis.

It is an aim of the present invention to provide an apparatus for capturing sufficiently accurate images of microbial growth in order to assist in providing a microbiological assessment.

Before turning to a summary of the present invention, it must be appreciated that the above description of the prior art has been provided merely as background to explain the context of the invention. It is not to be taken as an admission that any of the material referred to was published or known, or was a part of the common general knowledge in Australia or elsewhere.

SUMMARY OF THE INVENTION

The present invention provides apparatus for use in analysing microbial growth on a solid culture medium in a culture plate, the apparatus including:
  an image capture device,
  a support for supporting the culture plate for the image capture device to capture an image of the solid culture medium and any microbial growth,
  a ring light between the image capture device and the support, for diffusely illuminating one side of the culture plate, and
  a frame for positioning the image capture device, support and ring light relative to each other, wherein the frame defines a cavity such that the support supports the culture plate between the image capture device and the cavity, and the cavity has a height selected so that the cavity provides a black background for the image of the solid culture medium and any microbial growth, and wherein the frame includes a wall of the cavity having said height selected so that light emitted from the ring light falls on the wall of the cavity to provide the black background.

It will be appreciated by those persons skilled in the art that, with respect to the phrase "on a solid culture medium", the word "on" is used to encompass microbial growth both upon the surface of the solid culture medium and within the solid culture medium. The term "solid culture medium" will hereinafter often be simply referred to as "medium" in the specification. For example, it will be appreciated that a microbiological sample, hereinafter often referred to simply as a "sample", can be dispensed either upon the surface of the medium or within the medium so that microbial growth can be grown following the inoculation and incubation of the medium with the sample. That is, the microbial growth on the medium results from the inoculation and incubation of the sample, such as a urine sample, an enteric sample, a blood sample, a lymph sample, a tissue sample, a water sample, a food sample or other relevant sample, on the medium.

In addition, it will also be appreciated by those persons skilled in the art that the medium will usually be, for example, agar and will usually be contained in a container such as a plate, and, in a more specific example, a Petri dish, which may have a lid.

The combination of the medium and the plate is hereinafter referred to throughout the specification as a "culture plate" which might sometimes be referred to in the art as an "agar plate".

The apparatus has been found, in an exemplary example, to provide sufficiently accurate images of microbial growth on the medium in order to provide a microbiological assessment. This assessment may be performed manually by a skilled laboratory technologist. Alternatively, the assessment may be automated and performed using a classifier that has been trained using a machine learning algorithm. Images obtained using the apparatus may be processed and used as input into the classifier. An example of such a classifier is described in the co-pending International application of the same Applicant and with the same filing date titled "Method and Software for Analysing Microbial Growth", the contents of which are herein incorporated by reference.

The image capture device may be a digital camera and lens. For example, a high resolution digital colour camera in combination with an appropriate lens has been found to provide quality images of the plates. Image capture devices having many different specifications are suitable for the purpose as would be understood by the skilled addressee.

The microbial growth may include, for example, one or more bacterial growths, fungal growths, viral plaques or protist growths and the growth may take the form of a colony, mycelium, hypha, plaque or other visible microbial structure. In some embodiments, each microbial growth may be growth that originates from a single microbe (such as where a sample is applied to a medium in a diluted manner such that individual microbes are separated).

The medium may include any medium which supports the growth of a microbe. As such, a medium may contain one or more microbial nutrients including, for example, a carbon source, a nitrogen source, essential elements and/or essential vitamins. The medium will also typically contain a gelling agent including, for example, gelatine, agar, gellan gum, agarose or agargel.

In some embodiments, the sample for analysis is disposed on more than one culture plate or a split culture plate having more than one segment. In these embodiments, the analysis of microbial growth is performed by taking images across the different culture plates, or segments, and the results of the pixel classifications are analysed as above so that a microbiological assessment can be made based on a comparison of microbial growth on the different culture plates or segments.

In some embodiments, the medium may include a selective culture medium, which is generally known in the art to include media with restricted nutrient compositions, media containing an antibiotic, or the like, that allow for the growth of some microorganisms while preventing growth of other microorganisms.

The use of a ring light for diffusely illuminating one side of the culture plate assists a classifier in distinguishing between light reflected from the medium (which may be classified as background) and microbial growth. The reference to a "side" of the culture plate is to be taken to refer to any side including front, back, left, right, top or bottom side of the culture plate. In a preferred embodiment, the ring light diffusely illuminates the top of the culture plate, e.g. the surface of the medium on which microbial growth is present.

The medium has a meniscus around its outer periphery where it contacts the walls of the culture plate. As the surface of the medium may be glossy, this meniscus may generate a specular reflection in an image taken by the image capture device. If point lights were used to illuminate the culture plate, these reflections may be interpreted as bacterial colonies by the classifier. By using a ring light with diffuse illumination, the light source appears in the image as a continuous smooth line. Thus, any reflection from the meniscus is seen as a continuous smooth line that can be distinguished by the classifier from real bacterial colonies.

The ring light may include a plurality of LEDs arranged in a circular array and a diffuser associated with the LEDs. Alternatively, the LEDs may themselves produce diffuse light and a separate diffuser may not be required. LEDs may be evenly spaced around the array in a single ring or in multiple rings. In one arrangement, the LEDs may be selectively illuminable so that, for example, only half or a smaller fraction of the ring light is activated at one time. This may provide angled lighting of the culture plate, and may be useful in highlighting surface topography of the medium. To ensure a uniform distribution of light intensity the number of LEDs in the array may be greater than 50, preferably greater than 180 so that a LED is spaced every 2 degrees. This is further assisted by the diffuser to smooth out the light distribution. In other alternatives, the ring light may be a fluorescent light or a plurality of fibre optic sources with a diffuser.

The ring light may be located relative to the support so that specular reflection of light from the ring light from a central surface of the medium is at an angle that is not captured by the image capture device. For example, the ring light may have a width or diameter of between 120 and 250 mm and may be positioned between 30 and 50 mm above the support. As a culture plate is typically circular, generally having a diameter of between 80 and 110 mm, light emitted from the LEDs will strike the central surface of the culture plate at such a low angle that it does not reflect into the camera lens. This prevents reflections of the LEDs from appearing in the image, producing a higher quality image for producing inputs to the classifier and hence a more accurate assessment.

In addition to the ring light, the apparatus may further include a lighting device for illuminating another side of the culture plate. For example, if the ring light illuminated the top of the culture plate, the lighting device may illuminate the side or bottom of the culture plate. In one arrangement, the lighting device may be a low angle side light. In another arrangement, the lighting device may be a flat panel light for illuminating the bottom of the culture plate. The lighting device may include a plurality of LEDs and a diffuser associated with the plurality of LEDs. The LEDs may be arranged in a square or rectangular shape to create the flat panel light.

Use of lighting from different sides of the culture plate enables the image capture device to capture different clinically relevant characteristics of colonies on the culture plates. A sequence of images may be captured under several configurations of lighting. These lighting configurations include top light, to visualise the colony colour; bottom light to visualise the colour changes in the volume of the medium (e.g. agar) below and around the colony, and low-angle side-light to visualise any surface topography such as dimples or granularity. To capture the images no physical backgrounds need to be moved—the lights may be separately illuminated by electrical switching. It will be appreciated, however, that not all lighting configurations need be used to obtain a meaningful microbiological assessment.

Where a bottom light (for example the flat panel light) is used, image capture may be facilitated using a support that is transparent. By "transparent" it is meant that light from the lighting device may pass through the support and be captured by the image capture device. In one embodiment, the support may be a glass stage. Other forms of support, such as a wire frame or short "fingers" around the edge of the culture plate could also achieve the same effect.

The support ideally positions the culture plate immediately below the image capture device with its field of view directed to the culture plate. As well as capturing the culture plate in an image, the image capture device may also capture the area about the culture plate. The apparatus may be arranged to include in the area about the culture plate, in the field of view of the camera, various optical test features, such as a focus target, colour correction patches or alignment guides.

A culture plate to be imaged may be positioned manually on the support by an operator, and the support may include one or more transparent positioning elements to assist in positioning the culture plate. These elements may define a position on the support such that the culture plate is precisely located in the field of view of the camera. The use of transparent elements maintains uniformity in lighting in the vicinity of the elements. The transparent positioning elements may be triangular shaped with the apex of the triangle pointing towards the centre of the support. Thus, the culture plate may be positioned so that the apex of the triangles touches the circumference of the culture plate. Transparent triangular elements were found to produce minimal disturbance to the uniform illumination. The transparent elements may alternatively have a different shape or may be posts protruding from the surface of the support.

Other devices for manual placement include a circular recess that the culture plate drops into, or a series of fine wire fingers that touch the external wall of the culture plate. In another embodiment, the culture plate to be imaged may be positioned automatically, by a robotic placement device. In this case, the robotic device may be programmed to position the culture plate in a predetermined position, and no physical stops would be required.

The frame may be a rigid structure that positions the image capture device, support and ring light relative to each other. The frame may be constructed in multiple parts that are connected together by bolts, screws or any suitable connection means. Alternatively, the frame may be formed in one piece by the use of suitable metal working techniques or moulds. The frame may play a part in light proofing the apparatus as will be described below.

The frame may include an opaque cover for supporting the support. By "opaque" it is meant that little or no light can pass through the cover. For example, the cover may be a flat piece of aluminium or other metal that extends across the width of the frame. The opaque cover may include a hole that the glass stage sits over so that a bottom light is still able to illuminate the bottom side of the culture plate through the opaque cover. The hole in the light proof cover may further have a width that is less than the width of the ring light so that light from the ring light does not reflect off the bottom of the frame and back up through the culture plate. In this way, when the ring light is illuminated, there is no discernable light coming through the medium, by scattering from any surfaces surrounding or below the culture plate, or from any light scattered and transmitted by the medium (e.g. translucent agar) itself. The hole may have a shape to match the shape of the ring light, such as circular, but the shapes need not match. To capture an image of the whole culture plate, the hole should be larger than the size of the largest culture plate to be imaged.

In an embodiment, the frame defines a cavity such that the support supports the culture plate between the image capture device and the cavity. The effect of the cavity is to provide a "black background" for capturing high contrast images of the translucent culture plate illuminated by the ring light. When the ring light is illuminated, and any other lighting devices are off, the frame around the culture plate (e.g. the opaque cover) prevents light from the ring light from falling on the bottom of the cavity. This is achieved by selecting the height of the cavity so that the shadows of the frame cover the bottom of the cavity and the light from the ring light hits, and is absorbed by, the edges of the cavity.

The frame may further include light baffles that form a wall of the cavity. These baffles may completely surround the cavity below the culture plate, and may have their internal surfaces blackened by painting, or by covering with a textured light absorbing material such as black velvet or an open-celled porous black foam material.

The cavity or void looks like a black background and has the advantage that it can be illuminated without physically moving any components of the apparatus. The cavity may be sealed, for example by the frame and support, to prevent material from falling into it. For example, where the support is a glass stage this may extend the full width of the frame to allow easy cleaning and prevent contamination.

The frame may serve a further purpose of forming an opaque (light proof) enclosure around the apparatus. The frame may be made from, for example, metal bars or metal sheet. The internal surfaces of the frame may be blackened to reduce reflection of any stray light from the surfaces. The frame may include an access door for placing the culture plate on the support. The door may be hinged and have flexible, light-tight seals so that, when closed, it does not allow a significant amount of light to enter the enclosure.

Although the spatial references of the apparatus components described above are based on a culture plate being seated in the apparatus in an upright orientation, with the surface of the medium being generally flat and horizontal, it will be appreciated that the components of the apparatus may arranged in other orientations. References to "above", "below", "up" or "down" are not to be taken as limiting the positioning of the components but are merely provided for ease of explanation. For example, the culture plate may be seated in the apparatus so that the surface of the medium is vertical, facing downwards or in any other orientation. In these cases, the components of the apparatus would be correspondingly arranged to provide appropriate lighting and imaging of the culture plate.

In yet another embodiment, the apparatus may further include means for changing the position of the ring light relative to the support. The ring light may therefore be raised or lowered to allow large robotic mechanisms to enter or to provide different lighting angles for different plate types. The means for changing the position of the ring light also allows additional image data for a culture plate to be obtained by taking images with the ring light at different heights. Mechanisms for raising and lowering the ring light may include a motorised rack and pinion device between the right light support and the frame, or a set of equi-spaced suspension cables attached to the ring light support which are wound in or out via an electric motor.

BRIEF DESCRIPTION OF THE DRAWINGS

Embodiments of the present invention will now be described, by way of example only, with reference to the accompanying drawings. It is to be understood that the particularity of the drawings does not supersede the generality of the preceding description of the invention.

DETAILED DESCRIPTION OF AN EMBODIMENT

Figure 1:
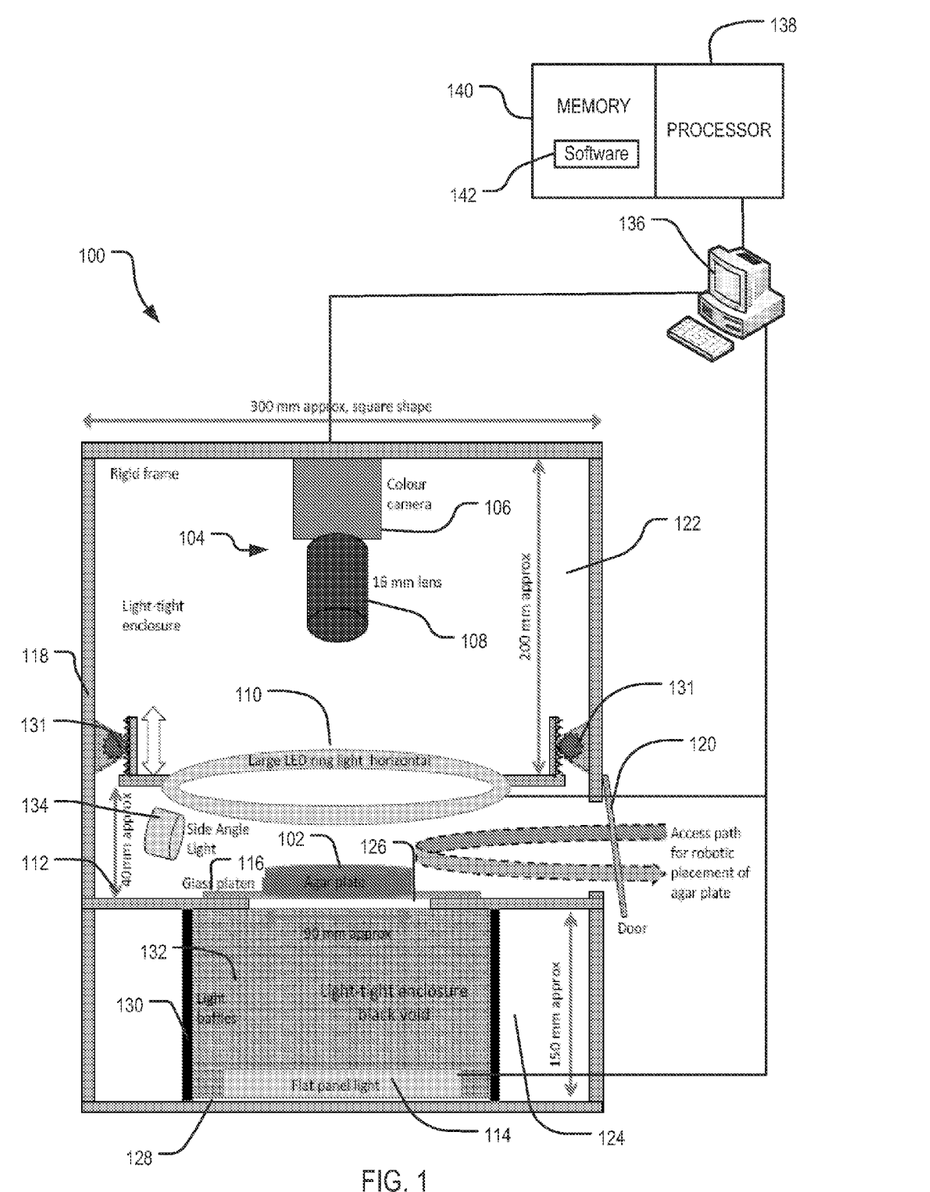
FIG. 1 is a schematic diagram of an apparatus for use in analysing microbial growth on a solid culture medium in a culture plate.

FIG. 1 shows an embodiment of an apparatus 100 for use in analysing microbial growth on a medium in a culture plate 102 in the form of an agar plate. The apparatus 100 includes the following components:

An image capture device 104 in the form of a high resolution digital camera 106 of machine vision quality with an appropriate fixed focal length lens, 108. The camera 106 is positioned about 200 mm above a ring light 110.

The ring light 110 has a large diameter relative to the diameter of the culture plate 102. In this example, the ring light has a diameter of 180 mm. The ring light 110 contains several hundred white LEDs arranged in a circular array and a diffuser. This light provides low angle, diffused side lighting to enable the culture plate to be uniformly illuminated. The ring light 110 is positioned around 40 mm above an opaque cover 112 that forms part of the frame 118, and thus about 30 mm above the culture plate 102. The positioning of the ring light 110 so that light from the white LEDs impinge on the surface of the culture plate 102 at a low angle prevents a specular reflection of the LEDs from a central surface of the medium being captured by the image capture device 104.

A lighting device 114 in the form of a flat panel light based on an array of white LEDs behind a diffuser. The lighting device 114 is located about 150 mm below the opaque cover 112. This distance is chosen so that light from the ring light 110 falls on the baffles rather than the light 114, to reduce rear illumination of the culture plate 102.

A support 116 for supporting the culture plate 102 in the direct field of view of the image capture device 104. The support 116 is a transparent glass stage that is 3 mm thick. The glass may be replaced if it becomes scratched over time. The support 116 includes two or more triangle shaped transparent positioning elements for positioning the culture plate 102 on the support. The apexes of the triangles point towards the centre of the support for placement of the culture plate 102 so that the apexes touch the circumference of the culture plate 102.

A frame 118 positions the image capture device 104, support 116, ring light 110 and lighting device 114 relative to each other. The frame 118 is made of an opaque material, such as sheet metal or plastic, which reduces the amount of light entering the apparatus 100. The internal surfaces of the apparatus 100 are blackened where possible to reduce reflection of light from the internal surfaces into the lens 108.

The frame 118 includes a door 120 providing an access patch for a human operator to place the culture plate 102 on the support 116. Alternatively, a robotic plate-handling device may use the access path to place the culture plate 102 precisely on the support 116 for imaging, and then to remove the culture plate to a designated output channel/slide. For example, the culture plate may be placed in an output channel representing one of the up to four categories described above.

The opaque cover 112 is an aluminium plate that extends across the width of the frame 118 and effectively splits the frame 118 into a top enclosure 122 and bottom enclosure 124. The opaque cover 112 includes a hole 126 to allow light from the lighting device 114 to transmit through to the culture plate 102. The width of the hole 126 is just slightly larger than the width of the culture plate 102 (which is 90 mm in this example and is typically between 88 and 100 mm) and is less than the diameter of the ring light 110. This prevents light emitted from the ring light 110 from reflecting from the bottom surface 128 of the frame 118 or the surface of the flat panel light 114 and back through the culture plate 102.

The frame 118 also includes light baffles 130 positioned below the opaque cover 112.

Means 131 for changing the position of the ring light 110 relative to the support 116 are also provided in the form of a rack and pinion assembly.

The frame 118, opaque cover 112 and light baffles 130 define a cavity 132 such that the support 116 supports the culture plate 102 between the image capture device 104 and the cavity 132. The support (glass stage) 116 seals the cavity 132 and prevents unwanted material from falling into the cavity 132. When the ring light 110 is illuminated and the lighting device 114 is off, the opaque cover 112 prevents light from the ring light 110 from illuminating visible areas of the cavity 132. In this configuration, the cavity 132 looks like a black background.

A side angle light 134 is used to illuminate the culture plate 102 from an angle to highlight any surface topography on the agar, such as dimples or a granular texture. An alternative to the side angle light 134 is to activate only some of the LEDs in the ring light 110, such that the culture plate 102 is illuminated from one direction only.

A processing means such as a computer 136 is connected to the image capture device 104, the ring light 110 and the lighting device 114 via a physical or wireless interface. The computer 136 may include a processor 138 and memory 140 storing software 142 for activating the different components, capturing raw data and processing the data.

A library of images, metadata and other information may be stored at the computer 136, or may be accessible at the computer 136 via a network. Similarly, the LIMS may be accessed via the computer 136.

It will be appreciated that different components may be substituted for any of the above described components of the device, and that the distance between components and position of components may be adjusted. For example, although the camera 106 and lens 108 are shown inside the frame 118, in another example, they could be positioned outside the frame 118, with the lens 108 protruding through a hole in the top surface of the frame 118. Also, the width of the frame 118 could be decreased to reduce the overall size of the apparatus 100.

An image acquisition process using the apparatus 100 will now be described. This process may be suitable for obtaining images for use in classifying microbial growth on the culture plate 102 using a trained machine learning classifier, or in training such a classifier. A manual process will be described, where many steps are performed by a human operator, but it will be appreciated that many of the steps of the process may be automated and performed in software or by a robotic device.

Firstly, an inoculated and incubated culture plate 102 is positioned on the support 116, within the triangular stops, by a user. Culture plates 102 are generally stored within a laboratory with the agar facing down (to prevent condensation on the lid from falling on to, and damaging, the agar surface), so positioning the culture plate 102 on the support may include removing a lid of the culture plate 102 and rotating the culture plate so that the agar is facing upwards.

Figure 2A:
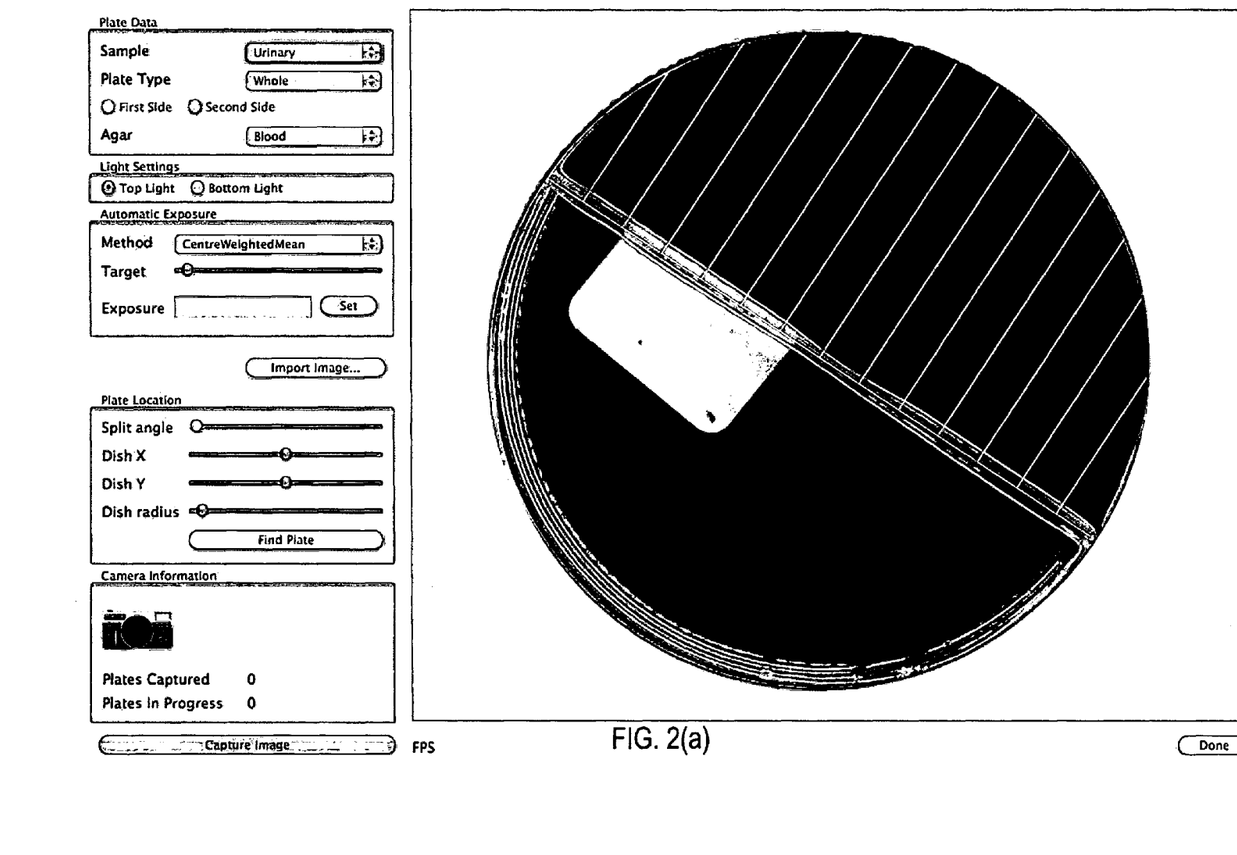
FIG. 2(a) is a screen shot of a GUI for a user to capture images.

The software 142 is activated to begin the image capture process. The software 142 requires the user to scan a barcode on the culture plate 102, or enter a number manually. The barcode links to a sample ID, which links the culture plate to a particular sample and, via a LIM system, to a particular patient. Once the barcode has been entered, a live video preview of the camera output appears in the window shown in FIG. 2(*a*). The user may adjust the location of the culture plate 102 or the focus or aperture of the lens 108, based on the feedback provided by the live video stream.

Figure 2B:
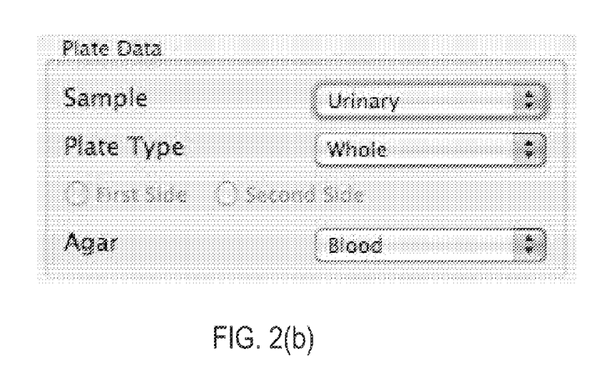
FIGS. 2(b) to 2(e) are close up views of details on the left side of the screen shot of FIG. 2(a).

The user is then required to select the culture plate type (e.g. split or whole), sample type (e.g. urinary, enteric, blood or tissue) and agar type(s) (e.g. blood or chromogenic). An example of a plate data selection options is shown in FIG. 2(*b*) and at the top left of FIG. 2(*a*). In an alternative, rather than requiring the user to select the culture plate, sample and agar type, this information could be extracted from the LIM system, based on the barcode entered.

Figure 2C:
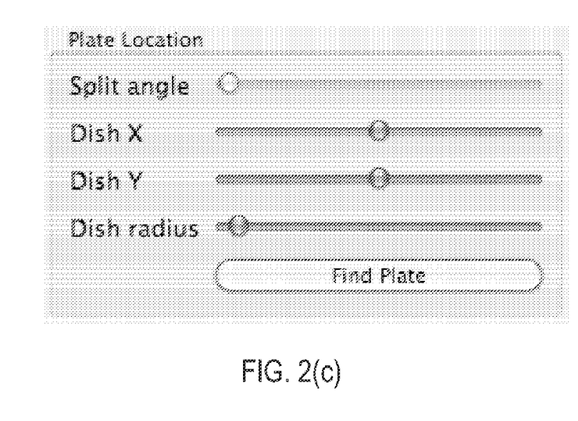
Figure 3:
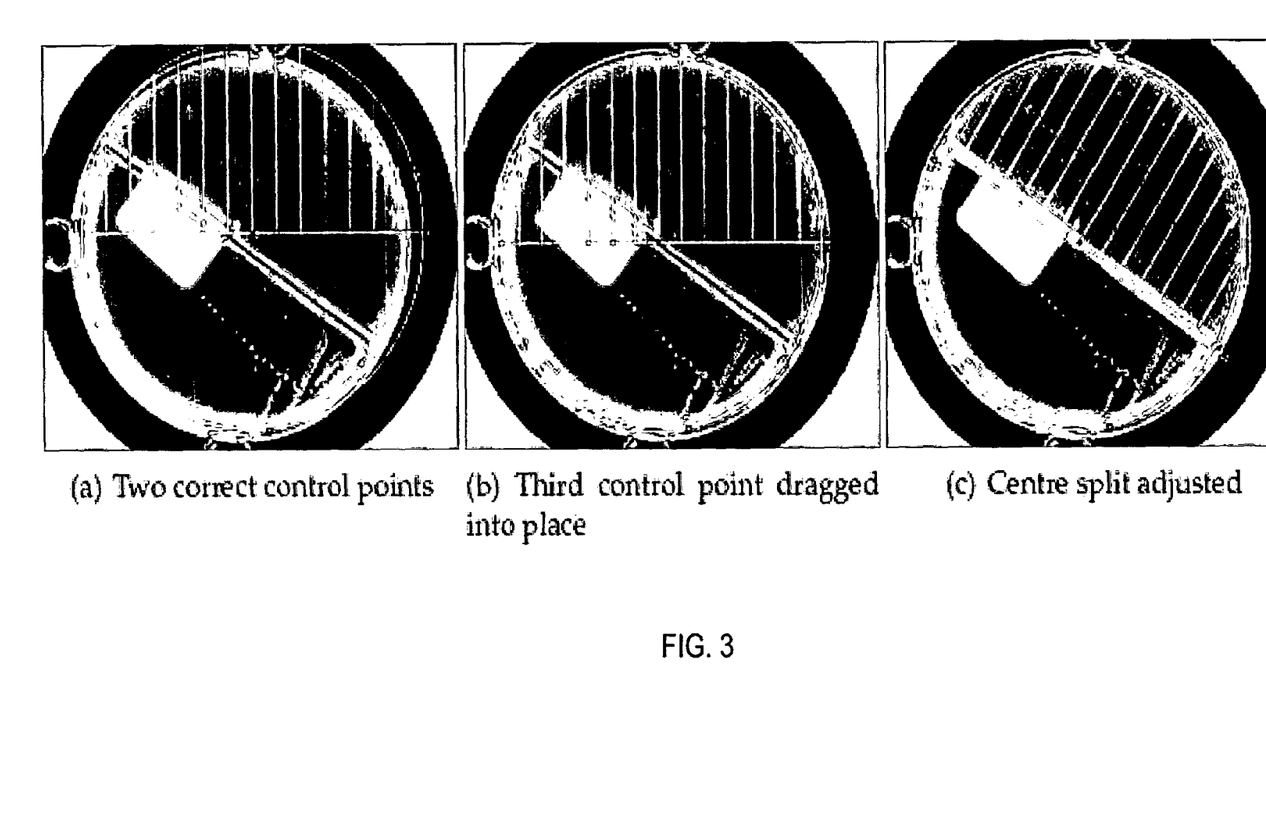
FIG. 3 is a series of screen shots showing a GUI for entering the position of a culture plate in an image.

After this data has been entered, the culture plate position is entered. There are two ways that this information can be entered by the user. The first is through a traditional set of sliders, which allow entry of the x, y location of the dish, along with its radius. If the dish is a split dish, the user must also enter the location of the split. An example of this is shown in FIG. 2(*c*) and the bottom left of FIG. 2(*a*). The second method is through manipulating a set of markers over the live video preview. The user places the circle around the agar via three points, which the user is able to move interactively. These three points uniquely define a circle. A fourth control point allows the user to specify the location of the central split, if appropriate. Such control points are quick and easy to place very accurately. FIG. 3 shows an example of how such an interaction might occur. In a system with a robotic culture plate placement, the location of the culture plate will be known, and the location of the split can be computed.

The exposure and light settings may be drawn from a database on the basis of the culture plate, sample and agar type(s) selected.

Figure 2D:
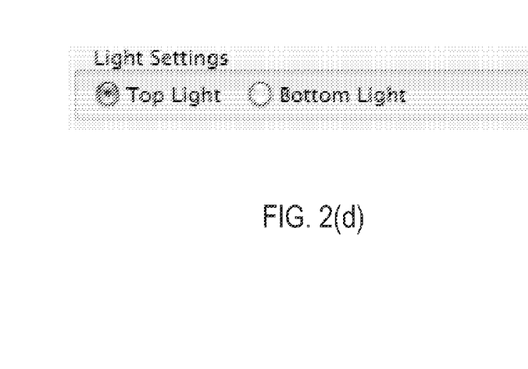
Figure 2E:
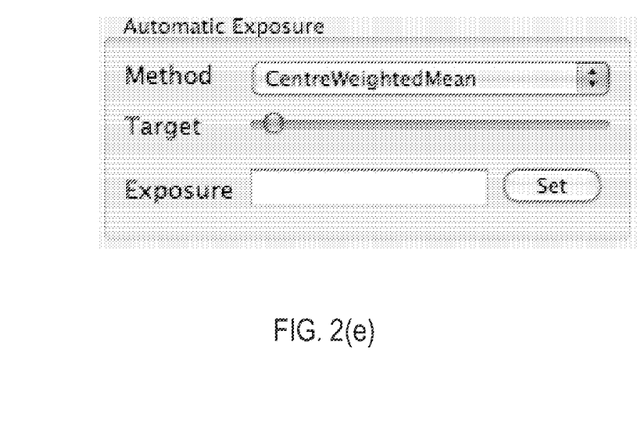

Correct exposure is important to good quality image capture. During testing of the camera 106, it was determined that separate exposures are required for each side of a split culture plate, owing to the different opacities of the different types of agars they may contain. The choice of lighting will also heavily influence the required exposure settings, so the user is also able to preview the image in any available configuration, with top or bottom lights activated. FIG. 2(*d*) shows radio buttons that may be used to select either the top light or bottom light to activate. Although not shown, the user may alternatively choose the side angle light to activate.

The exposure settings may be adjustable by the user, for example using a range of automatic exposure algorithms that may be selected using a drop down menu such as shown in FIG. 3(*e*). Each of the automatic exposure algorithms has the same core. Given a target brightness, $b_{tgt}$, and a measured brightness, $b_{meas}$, the new exposure, $e_{new}$, is calculated as:

$$\alpha = \frac{b_{tgt}}{b_{meas}}$$

$$e_{new} = \begin{cases} 0.8\ e_{old} & \text{if } b_{meas} > 1 \\ 0.5\ e_{old} & \text{if } \alpha < 0.5 \\ 2\ e_{old} & \text{if } \alpha > 2 \\ \alpha\ e_{old} & \text{otherwise} \end{cases}$$

In other words, if the brightness is too high (the image is saturated), unconditionally drop the exposure to 80% of its previous value. If this is not the case, the change is then clamped to be between 0.5 and 2. The adjustment stops if two successive exposure settings are within 10 microseconds of each other. Both brightness measures are typically represented as a number between zero and one, where zero is black (no brightness) and one is white (full brightness).

The difference between the various automatic exposure algorithms is in how they compute the brightness of the current image. Different algorithms that may be used include:

Mean—In this mode, the mean brightness of all pixels in the image is computed.

Centre-Weighted Mean—Centre-weighted mean computes the mean brightness of all pixels, but gives those pixels within $\sqrt{8} \times r$ of the centre additional weight (each centre sample is counted 8 times).

Spot—This method again computes a mean brightness, but only of those pixels within $\sqrt{20}\%$ of the centre. This method is not as appropriate for agar plates, since the centre of the image has no special meaning.

Median—This method computes the median brightness across the image via a histogram calculation. Each bin of the histogram is 4 levels wide, hence if the input images are 16-bits the histogram has 16384 bins. The true bit-depth of the images could also be read from the camera and provided to the algorithm.

Green—This method is the same as Mean, but uses the green channel alone to compute the brightness. This is advantageous for two reasons. First, there are twice as many true green pixels in a Bayer mosaiced image as red or blue. Second, the human eye is sensitive to green, so using it to adjust the images should provide a conceptually high quality image.

The software 142 may further include processes for assisting the user to select good exposure settings, for example, by pulsating pixels between their normal colour and red. This helps to identify overexposed, or saturated, pixels, which can be rectified by reducing the target image brightness.

Figure 4:
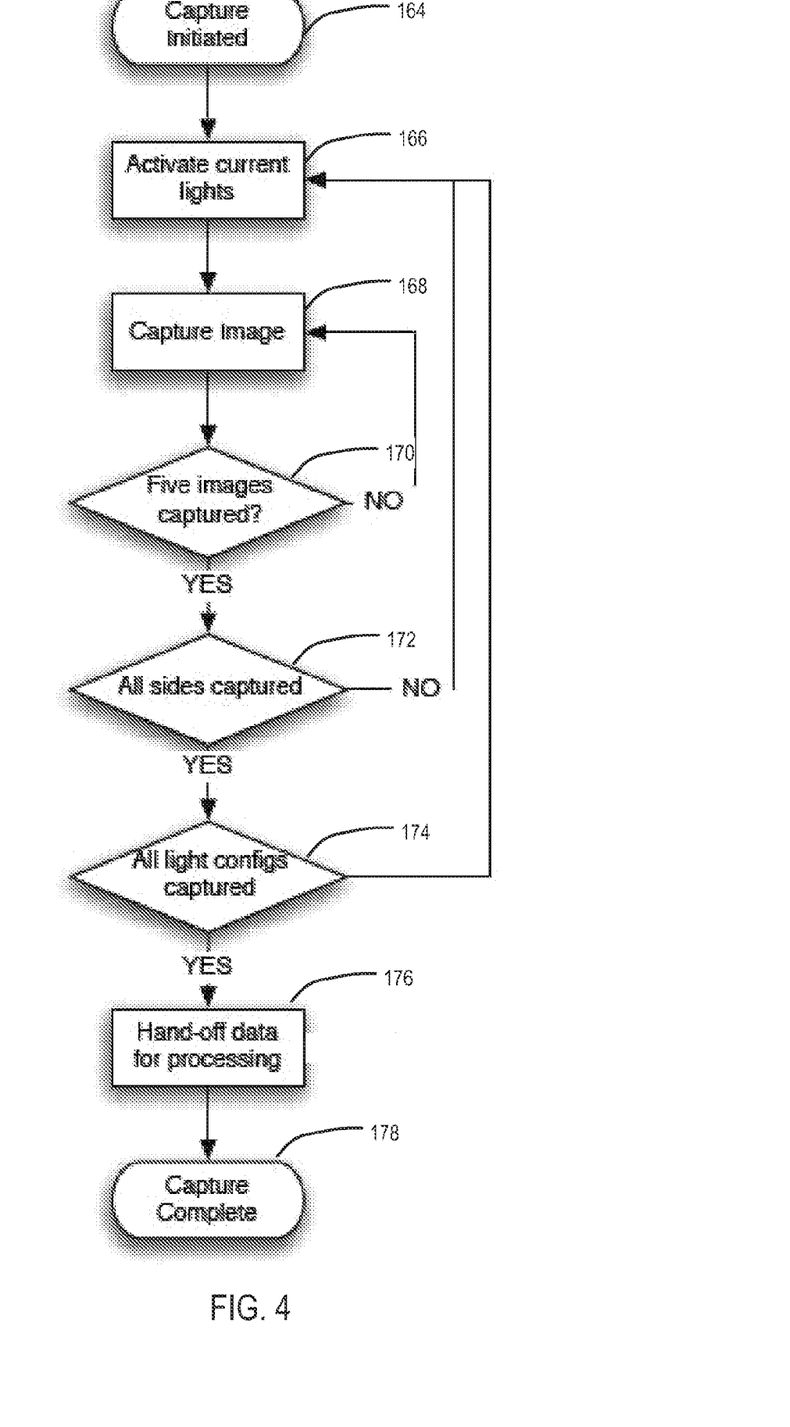
FIG. 4 is a flow chart showing a method for capturing an image of microbial growth on a solid culture medium.

Once the exposure settings are finalised for a given lighting configuration, image capture is performed using a method shown in FIG. 4. At step 164, capture is initiated, at step 166 the lighting configuration (e.g. the ring light 110) is activated. The image is captured at step 168 by image capture device 104 using this lighting configuration. Image capture is repeated five times for each culture plate, each time having the same exposure (step 170). The process is repeated for the other side of the culture plate in the case of a split culture plate (step 172) and for other lighting configurations, e.g. for the bottom lighting device 114 (step 174). At step 176, the captured images are handed off for data processing and then image capture is complete (step 178).

The image capture device may capture five images into a buffer with a first lighting configuration (e.g. top light illuminated) and then another five images with the second lighting configuration (e.g. bottom light illuminated). If the culture plate is a split culture plate with multiple sides, then these are also processed in the same manner. Exposure settings are loaded from the database and correct exposure is determined prior to each capture. For a split culture plate, capturing a single culture plate may thus require 5×2×2=20 images, which would take around 2 seconds, assuming that the camera 106 operates at 9 frames per second.

Once the images have been captured, they may be handed off to a separate thread of execution for asynchronous processing. The capture window then reverts to waiting for a barcode to be entered. Each time a culture plate image is captured, the image, along with any salient metadata is saved in the library. After capture, the culture plate 102 is removed from the apparatus 100 through the door 120. The raw data from the image capture device 104 is processed to obtain more accurate image data for the sample that can be used as input to analysis software.

Images captured may be stored in an electronic library, the LIMS or another dedicated image storage database. Other metadata such as the exposure time, date of capture, light information, colour transform used to correct the image and camera data may be stored in association with the image.

It will be appreciated that although in the software described above, a user is required to position the culture plate and enter metadata, this process could be automated. For example, a robotic arm may place the culture plate on the support before image capture and remove it after image capture. The software could automatically detect the position of the culture plate in the image and whether it is split or whole. A robotic system may be used to read an identifier or barcode on the culture plate. The barcode or other identifier may enable access to information such as culture plate type, sample type and agar type so that this information does not need to be entered by the user. In a version of the software aimed at fully automatic processing, the user would not adjust the exposure or target brightness settings.

It is to be understood that various alterations, additions and/or modifications may be made to the parts previously described without departing from the ambit of the present invention, and that, in the light of the above teachings, the present invention may be implemented in a variety of manners as would be understood by the skilled person.

The invention claimed is:

1. Apparatus for use in analyzing microbial growth on a solid culture medium in a culture plate, the apparatus including:
   an image capture device,
   a support for supporting the culture plate for the image capture device to capture an image of the solid culture medium and any microbial growth,
   a ring light between the image capture device and the support, for diffusely illuminating one side of the culture plate, and
   a frame for positioning the image capture device, support and ring light relative to each other, wherein the frame defines a cavity such that the support supports the culture plate between the image capture device and the cavity, and the cavity has a height selected so that the cavity provides a black background for the image of the solid culture medium and any microbial growth, and
   wherein the frame includes a wall of the cavity having said height selected so that light emitted from the ring light falls on the wall of the cavity to provide the black background.

2. Apparatus according to claim 1, wherein the ring light includes a plurality of LEDs arranged in a circular array.

3. Apparatus according to claim 2, further including a diffuser associated with the plurality of LEDs.

4. Apparatus according to claim 1, wherein the ring light is located relative to the support so that specular reflection of light from the ring light from a central surface of the solid culture medium is at an angle that is not captured by the image capture device.

5. Apparatus according to claim 4, wherein the ring light is positioned between 30 and 50 mm above the support.

6. Apparatus according to claim 1, further including a lighting device for illuminating another side of the culture plate.

7. Apparatus according to claim 6, wherein the lighting device is a flat panel light including a plurality of LEDs and a diffuser associated with the plurality of LEDs.

8. Apparatus according to claim 7, wherein the flat panel light illuminates a bottom side of the culture plate to facilitate visualization of color changes in the solid culture medium from the image.

9. Apparatus according to claim 1, wherein the support is transparent to light transmitted through the culture plate.

10. Apparatus according to claim 9, wherein the support includes one or more positioning elements for positioning the culture plate on the support.

11. Apparatus according to claim 10, wherein the support includes a placement device configured to position the culture plate in a position for the image capture device to capture the image of the solid culture medium and any microbial growth.

12. Apparatus according to claim 9, where the support includes a plurality of spaced apart fingers extending from a periphery of a circular hole supporting at least an edge of the culture plate.

13. Apparatus according to claim 1, wherein the frame includes an opaque cover for supporting the support.

14. Apparatus according to claim 13, wherein the opaque cover includes a hole having a width that is less than a width of the ring light.

15. Apparatus according to claim 14, wherein the width of the hole is selected so that light emitted from the ring light falls on the wall of the cavity to provide the black background.

16. Apparatus according to claim 13, wherein the ring light has a width of between 120 and 250 mm.

17. Apparatus according to claim 1, wherein the frame includes an access door for placing the culture plate on the support in the position for the image capture device to capture the image of the solid culture medium and any microbial growth.

18. Apparatus according to claim 1, further including a motorized rack and pinion device between the right light and the support for changing the position of the ring light relative to the support.

19. Apparatus according to claim 1, wherein the wall includes a light baffle.

20. Apparatus according to claim 1, further including a set of equi-spaced suspension cables attached to the ring light and the support which are wound in and out via an electric motor for changing the position of the ring light relative to the support.

* * * * *